US00PP15665P3

(12) United States Plant Patent
Olbricht

(10) Patent No.: US PP15,665 P3
(45) Date of Patent: Mar. 15, 2005

(54) **VARIETY OF *PELARGONIUM* PLANT NAMED 'PACEYES'**

(50) Latin Name: *Pelargonium crispum*
Varietal Denomination: Paceyes

(75) Inventor: Klaus Olbricht, Dresden (DE)

(73) Assignee: Elsner pac Jungpflanzen Dresden, Dresden (DE)

( * ) Notice: Subject to any disclaimer, the term of this patent is extended or adjusted under 35 U.S.C. 154(b) by 46 days.

(21) Appl. No.: 10/456,175

(22) Filed: Jun. 6, 2003

(65) Prior Publication Data

US 2004/0250327 P1 Dec. 9, 2004

(51) Int. Cl.[7] ..... A01H 5/00
(52) U.S. Cl. ..... Plt./324
(58) Field of Search ..... Plt./324

*Primary Examiner*—Kent Bell
(74) *Attorney, Agent, or Firm*—Webb Ziesenheim Logsdon Orkin & Hanson, P.C.

(57) ABSTRACT

A new and distinct flowering *Pelargonium* plant with abundant purple colored flowers.

1 Drawing Sheet

Botanical classification: *Pelargonium crispum.*
Varietal denomination: 'Paceyes'.

BACKGROUND OF THE INVENTION

The present invention comprises a new and distinct cultivar of *Pelargonium crispum* hybrid known by the varietal name 'Paceyes'. The new variety was discovered in a selected breeding program in Dresden, Germany. The new variety is the result of a cross between two unnamed and unpatented selections from a collection of proprietary breeding plants. The flower habit and size of the new variety are similar to its parents but with different flower color and intensity of the eye. The new variety was first asexually reproduced in November 2000 by cuttings in Dresden, Germany. The new variety was grown in a warm greenhouse in January; then moved outside in February; then transferred to baskets in May. The new variety has been trial and field tested in Dresden and has been found to retain its distinctive characteristics and remain true to type through successive asexual propagations.

DESCRIPTION OF THE DRAWINGS

The accompanying photographic drawing illustrates the new variety, with the color being as nearly true as is possible with color illustrations of this type.

DESCRIPTION OF THE PLANT

Figure 1:
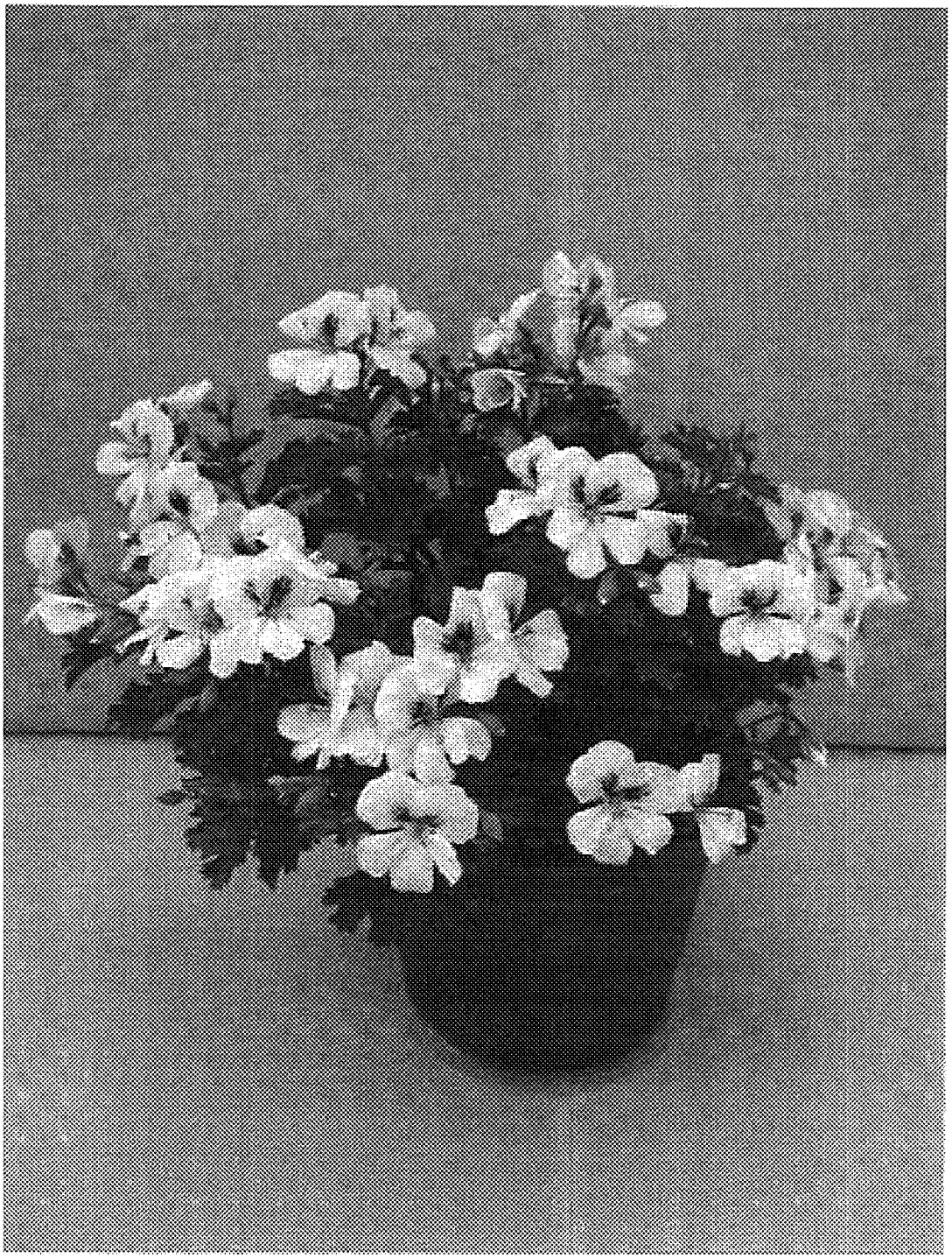

The following detailed description sets forth the characteristics of the new cultivar. The data which defines these characteristics were collected by asexual reproductions by carried out in a warm greenhouse in Dresden, Germany. Plants were 9 months old when described. The color readings were taken on a plant indoors under natural light. Color references are primarily to The R.H.S. Colour Chart of The Royal Horticultural Society of London.

PLANT

Form: Cascading; mounded.
Height: 10–12 cm from soil to top of foliage; 15 cm from soil to top of umbels.
Diameter: 30 cm.
Growth: Erect, well-branched.

Strength: Does not require artificial support; self-standing.
Foliage: No zonation.
Time to produce flowering plant: 3 months.
Time to develop roots: 3.5 weeks.
Description of roots: White; adventive.
Leaves:
*Size.*—Length: Approximately 2 cm. Width: Approximately 2 cm.
*Shape.*—Overall: Maple leaf like. Base: Open. Apex: Pointed.
*Margin.*—Bi-serrate.
*Texture.*—Hairy.
*Color.*—Upper surface: 137B. Lower surface: 138A.
*Ribs and veins.*—Venation: Net-like. Color: 143B.
Petioles:
*Color.*—143B.
*Length.*—Approximately 2 cm.
Stem:
*Length.*—10 cm.
*Color.*—143B.
*Internode length.*—1 cm.
*Lateral branch length.*—5 cm.

THE BUD (Measurements taken just prior to opening)

Shape:
*Cluster.*—Spindle.
*Individual bud.*—Elliptic.
Size:
*Cluster.*—Approximately 1.8×2.0 cm.
Individual bud:
*Length.*—8.0 mm.
*Width.*—4.0 mm.
Color: 141B.

INFLORESCENCE

Blooming habit: Umbels.
Size:
*Width.*—Approximately 5.5 cm.
*Depth.*—Approximately 2.7 cm.
Borne: Umbel; flowers on pedicel; pedicel on peduncle.

Number of flowers per umbel: 2–4.

Flowers:

*Form.*—Zygomorphic.

*Size.*—Diameter: Approximately 3 cm. Depth: Approximately 1 cm.

*Petals.*—Number per flower: 5. Color: Upper surface: 75C. Lower surface: 75C. Eye: 71A; seen from upper surface. Shape: Overall: Round to oval. Apex: Round; not pointed. Base: Pointed. Size: Length: 1.7–2.2 cm. Width: 0.7–1.3 cm. Margin: Entire. Texture: Smooth.

Sepals:

*Color.*—Upper surface: 143A. Lower surface: 143C.

*Shape.*—Overall: Pointed; narrow. Apex: Pointed. Base: Wider and not pointed.

*Size.*—Length: Approximately 0.9 cm. Width: Approximately 0.2–0.3 cm.

Pedicel:

*Length.*—Approximately 2.0 cm.

*Color.*—143B.

Peduncle:

*Length.*—3–3.5 cm.

*Color.*—143A.

Disease/pest resistance: No susceptibility to diseases or pests has been noted to date.

Flowering season: Summer.

Lastingness of bloom: About 10 days.

Lastingness of umbel: About 3 weeks.

REPRODUCTIVE ORGANS

Stamens:

*Anthers.*—0.1–0.2 cm long.

*Filaments.*—Length: 0.9 cm. Color: 63C.

*Pollen.*—Uncountable.

Pistils:

*Number.*—One.

*Length.*—1.1 cm.

*Stigma color.*—71A.

*Style.*—Length: Approximately 0.6 cm. Color: 66A.

*Ovaries.*—Superior; hairy; 0.1 cm; Greenish in color.

Seeds: Rarely present.

*Amount.*—5 per flower maximum.

*Size.*—3 mm.

*Color.*—Brown.

GENERAL CHARACTERISTICS

'Paceyes' has the following general characteristics.

1. Compact growth; cascading with age.
2. Able to cultivate in small pots.
3. Beautiful flowers.
4. Extremely high cutting yield.
5. Good branching.
6. Abundant flowers.

I claim:

1. A new and distinct variety of *Pelargonium* plant substantially as shown and described.

* * * * *